(12) United States Patent
Kleinberg et al.

(10) Patent No.: US 6,423,300 B1
(45) Date of Patent: Jul. 23, 2002

(54) COMPOSITIONS TO CONTROL ORAL MICROBIAL OXIDATION-REDUCTION ($E_H$) LEVELS

(75) Inventors: Israel Kleinberg, Smithtown; Milroy Codipilly, Coram, both of NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 09/506,662

(22) Filed: Feb. 17, 2000

Related U.S. Application Data (60) Division of application No. 09/077,249, filed as application No. PCT/US97/19598 on Oct. 23, 1997, which is a continuation-in-part of application No. 08/736,356, filed on Oct. 23, 1996, now abandoned.

(51) Int. Cl.[7] .............................. A61K 7/16; A61K 9/68; A61K 7/20; A61K 7/36; A61K 6/00
(52) U.S. Cl. .............................. 424/49; 424/48; 424/53; 424/401; 424/614; 514/900; 514/901; 514/902; 514/494
(58) Field of Search .............................. 424/53, 48, 49, 424/401; 514/494, 900, 901, 902

(56) References Cited

U.S. PATENT DOCUMENTS

| | | | |
|---|---|---|---|
| 4,022,880 A | 5/1977 | Vinson et al. | 424/49 |
| 4,339,432 A | 7/1982 | Ritchey et al. | 424/54 |
| 4,689,214 A | * 8/1987 | Niles et al. | 424/49 |
| 5,076,960 A | * 12/1991 | Hutchings et al. | 252/186.33 |
| 5,125,837 A | 6/1992 | Warrin et al. | 433/98 |
| 5,392,947 A | * 2/1995 | Gentile | 220/665 |
| 5,405,836 A | * 4/1995 | Richar et al. | 514/23 |
| 5,738,840 A | * 4/1998 | Richter et al. | 424/53 |
| 5,753,217 A | 5/1998 | Christopfel | 424/76.9 |
| 6,325,997 B1 | 12/2001 | Christopfel | 424/76.9 |

FOREIGN PATENT DOCUMENTS

WO  PCT/US97/19598  8/1798

OTHER PUBLICATIONS

Biosis Abstract, Abstract No. 97:450683, Waler S.M. The effect of some metal ions on volatile sulfur-containing compounds originating from the oral cavity, abstract, ACTA Odontologica Scandinavica. 1997, vol. 55, No. 4, pp. 261–264.
Oxyfresh, Health Professional Seminar, Dallas, TX, Jun. 2, 1995 (compilation, including): "The Oxyfresh® Vision", etc. (corporate information), pp. 1–8; "An Overview of Chlorine Dioxide", pp. 9–11; "Management of Breath Disorders", pp. 12–22 (Guillory, "The Science and Cure of Halitosis", San Antonio Medical Gazette 1994, vol. 15, No. 42, pp. 13–15; Kleinberg and Westbay [excerpts from reference 13 herein], pp. 16–22); "Oxyfresh® & Veterinary Medicine", pp. 23–32; "Building Your Business", (Oxyfresh®), pp. 33–57; Rechter, "Kiss Bad Breath Good–Bye", Dental Economics 1995, May: 105, p. 58; "Oxygene® product description", p. 59; Fluoride products literature, pp. 60–61.

(List continued on next page.)

*Primary Examiner*—Frederick Krass
*Assistant Examiner*—Donna Jagoe
(74) *Attorney, Agent, or Firm*—Darby & Darby (57) ABSTRACT

The present invention relates to an oral composition containing a zinc compound containing free available zinc ion and at least one stabilized or stable $E_h$ raising compound distributed in an oral vehicle. The present invention further relates to a method of inhibiting the formation of sulfur containing anions and preventing a reduction in the $E_h$ of the oral cavity. A method of reducing oral malodor and gingivitis and periodontitis is also provided by this invention.

31 Claims, 9 Drawing Sheets

OTHER PUBLICATIONS

Yaegaki, "Oral Malodor and Periodontal Disease", pp. 93–114.

Yaegaki et al., "Effect of volatile thiol compounds on protein metabolism by human gingival fibroblasts", *J. Periodont Res* 1992:27:553–561.

Niles and Gaffar, "Advances in Mouth Odor Research", *"Bad Breath Research Perspectives"*, Rosenberg (Ed.) 1995, Rainat: Tel Aviv University, pp. 124–141.

Kleinberg et al., *Oral Biology and Medicine*, vol. 1, Issue 4, pp. 247–259, 1990.

Fischman et al., "The Inhibition of Plaque in Humans By Two Experimental Oral Rinses" J. Periodontics 1973, 44:155–157.

Internaitonal Preliminary Examination Report for International Application No. PCT/US97/19598 date Aug. 17, 1998.

* cited by examiner

COMPOSITIONS TO CONTROL ORAL MICROBIAL OXIDATION-REDUCTION ($E_H$) LEVELS

This application is a division of Ser. No. 09/077,249 filed Jun. 10, 1998 which is a national stage of PCT/US97/19598 filed Oct. 23, 1997 which is a continuation-in-part of 08/736,356 filed Oct. 23, 1996, abandoned.

FIELD OF INVENTION

The present invention provides oral compositions comprising a zinc compound containing free available zinc and at least one stabilized or stable $E_h$ raising compound distributed in an oral vehicle. The present invention is further directed to a method of inhibiting the formation of anionic sulfur species in the oral cavity and preventing a lowering of the $E_h$ of the oral cavity. A method of simultaneously reducing oral malodor, gingivitis and periodontitis by preventing or reducing oral putrefaction is also provided by this invention.

BACKGROUND OF THE INVENTION

The hard and soft tissues of the mouth are covered with microbial populations that contain bacteria with different metabolic capabilities. The Gram-positive bacteria within these microbial populations readily catabolize carbohydrates to produce acids which attack the hard tissues of the oral cavity, resulting in the formation of dental caries lesions (cavities). In contrast, the Gram-negative bacteria, especially the anaerobes readily metabolize various amino acids contained in salivary (and to lesser extent other) peptides and proteins in the oral cavity to form end-products which favor the formation of oral malodor and periodontitis. This process of peptide, protein and amino acid degradation by the mouth bacteria is referred to as oral bacterial putrefaction. The mixture of malodorous compounds produced by the Gram-negative anaerobic bacteria during putrefactive degradation of proteins, peptides and amino acids include hydrogen sulfide, methyl mercaptan, and dimethyl sulfide (formed from the sulfur containing amino acids cysteine, cystine and methionine); indole and skatole (formed during the metabolism of tryptophan); cadaverine and putrescine (produced from lysine and ornithine); and butyrate and valerate (produced from the metabolism of other amino acids). The production of these malodorous compounds in the oral cavity results in a condition commonly referred to as oral malodor.

Hydrogen sulfide, methyl mercaptan, butyrate and propionate are putrefaction end-products that also have cell and tissue altering non-inflammatory roles in the periodontitis process. Hydrogen sulfide and methylmercaptan are compounds particularly effective in facilitating the oral epithelium penetrability of toxins and other large molecular weight compounds produced by Gram-negative bacteria, and leading to the inflammation and tissue degradation characteristics of gingivitis and periodontitis. Gingivitis is a condition in which the gingiva is red, swollen and bleeding. If left untreated, gingivitis may develop into periodontitis, a condition characterized by destruction of the periodontium, including epithelial attachment loss, periodontal membrane and ligament destruction, and loss of gingiva and alveolar bone. Severe periodontitis resulting in deep periodontal pockets may ultimately result in tooth loss.

Previous studies have largely focused on the use of germicidal agents to treat gingivitis-periodontitis and oral malodor. Until the findings by the present invention, previous studies have not recognized that gingivitis-periodontitis and oral malodor arise from a common process, oral bacterial putrefaction; also that this putrefaction can be inhibited by simultaneously lowering the ability of the oral bacteria to reduce the oxidation-reduction potential ($E_h$) of the oral cavity and at the same time, raising the existing $E_h$ to where the oral environmental $E_h$ is not conducive to oral putrefaction and oral disease production.

The metabolism and growth of anaerobic bacteria in the oral cavity is favored when the $E_h$ is lowered. The present invention has discovered that the oxidation-reduction potential ($E_h$) is a key regulating factor in oral bacterial putrefaction. The lowering of the $E_h$ of the oral cavity has been found to occur in two steps, a depletion of oxygen followed by the generation of electron rich compounds. The present invention has discovered from studies on the isolation and catabolism by the oral bacteria of nitrogenous substrates in human saliva that the primary compounds responsible for lowering the $E_h$ of the oral cavity are non-volatile sulfur containing anions derived largely from cysteine and cystine (Table 1). These include the anionic sulfur species, sulfide ($S^-$), hydrogen sulfide ($HS^-$) and methyl mercaptan ($CH_3S^-$). Such anions favor an ecological environment of reduction (lower $E_h$) that enables the Gram-negative anaerobic bacteria in the mouth to grow, engage in oral putrefaction and produce electron-rich compounds leading to and maintaining a prolonged lowering of the $E_h$ of the oral cavity and the undesirable conditions of oral malodor, gingivitis and periodontitis. A lower $E_h$ favors the oral bacterial putrefaction process whereas a higher $E_h$ is inhibitory.

TABLE 1

Lowest $E_h$ reached with the common amino acids when incubated with the mixed bacteria in salivary sediment.

| | $E_h$ (millivolts) | | |
|---|---|---|---|
| amino acids | Group A | Group B | Group C |
| alanine | 100 | | |
| arginine | | 25 | |
| asparagine | 70 | | |
| aspartic | 80 | | |
| cysteine | | | 20 |
| cystine | | | −10 |
| glutamic | | 30 | |
| glutamine | 100 | | |
| histidine | 70 | | |
| isoleucine | 115 | | |
| leucine | 110 | | |
| lysine | 95 | | |
| methionine | | | 20 |
| ornithine | | 55 | |
| phenylalanine | 100 | | |
| proline | 100 | | |
| serine | 115 | | |
| threonine | 110 | | |
| tryptophan | 85 | | |
| tyrosine | | 40 | |
| valine | 105 | | | salivary supernatant −25; water control 142

The present invention provides compounds that simultaneously (i) inhibit the formation of these electron-rich compounds and thereby prevent the $E_h$ from falling to harmful levels and (ii) react with any electron-rich compounds formed and by thus neutralizing them, raise the $E_h$ to safer levels. It has been surprisingly discovered in accordance with the present invention that an oral composition containing a zinc compound capable of providing free available zinc and a stabilized or stable $E_h$ raising compound can effectively prevent the lowering of the $E_h$. This is crucial to preventing oral bacterial putrefaction, the metabolic process that is the basis and that results in the development of both oral malodor and gingivitis-periodontitis.

Zinc compounds, hydrogen peroxide, and chlorine dioxide have each been used as therapeutic agents in oral compositions to destroy harmful bacteria involved in oral malodor and gingivitis-periodontitis formation. Previous studies where zinc has been identified as having anti-microbial and anti-plaque effects have made no distinction between zinc compounds where the zinc is freely available and where it is not. (See for example, U.S. Pat. No. 4,289, 755 to Dhabhar). The zinc species is an important element of this invention, since free available zinc (zinc ion) within the oral cavity is required to inhibit the $E_h$ lowering capability of a pathogenic, putrefactive microbiota. Zinc compounds used in the compositions previously described include compounds where zinc is not freely available. Zinc that is bound or complexed to various ligands and zinc species that have a low solubility and form precipitates are prevented from reacting with the $E_h$ lowering enzymes and products produced by the putrefactive microbiota and hence are poorly suited for the purposes of this invention.

The solubility for zinc compounds vary as shown in the table below.

Solubility of selected zinc compounds

| Compound | Formula | Solubility (g/100 cc) |
| --- | --- | --- |
| zinc chloride | $ZnCl_2$ | 432 @ 25° C. |
| zinc citrate | $Zn_3(C_6H_5O_7)_2$ | slightly soluble |
| zinc acetate | $Zn(C_2H_3O_3)_2$ | 30 @ 20° C |
| zinc lactate | $Zn(C_3H_5O_3)_2$ | 5.7 @ 15° C. |
| zinc salicylate | $Zn(C_7H_5O_3)_2$ | 5 @ 20° C. |
| zinc sulfate | $ZnSO_4$ | soluble |
| zinc oxide | $ZnO$ | 0.00016 @ 29° C. |
| zinc nitrate | $ZnNO_3)_2$ | infinitely soluble |

Data are from the *Handbook of Chemistry and Physics*, Chemical Rubber Company, 67th Edition CRC Press, Boca Raton, Fla., 1986–87.

It is evident from this table that the amount of zinc that will be soluble and available in the oral cavity for controlling pathogenic microbiota will vary considerably. Those zinc compounds that provide low levels of zinc ion in solution, such as zinc oxide, are unsuitable for the present invention. This distinction between the various zinc compounds was not recognized prior to this invention. In essence, in order to inhibit the $E_h$ from falling to harmful levels, it is essential that the zinc ions are freely available.

Previous studies have also identified hydrogen peroxide and chlorine dioxide as germicidal agents. The chlorine dioxide is usually derived from the chlorite ion. Hydrogen peroxide owes its germicidal activity to oxygen release and formation of free radicals which provides chemical and mechanical mechanisms for killing oral anaerobic bacteria and cleaning wounds and removing tissue and other debris from inaccessible areas (such as between the teeth). The release of oxygen from hydrogen peroxide is particularly pronounced in the presence of catalase, organic matter, metals and metal compositions. In this invention, this is inhibited from happening by use of chloride ion, so that the peroxide will serve as an $E_h$ raising compound rather than as a germicidal agent. U.S. Pat. Nos. 5,104,644, 5,174,990 and 5,310,546 to Douglas describe the use of hydrogen peroxide as such a germicidal agent. Specifically in the oral composition described by Douglas, hydrogen peroxide releases molecular oxygen in the presence of tissue catalase and peroxidase to act against the oral anaerobic bacteria. Previous studies do not stabilize the hydrogen peroxide so that it does not break down.

The oral composition described herein acts as an $E_h$ raising compound rather than one that results in formation of breakdown products. In this invention, degrading these species to produce a germicidal effect, is avoided. The hydrogen peroxide in the composition described herein is stabilized using chloride ion, an acidic pH, and avoiding mixing it with zinc ion until just before use.

Chlorine dioxide is an oxyhalogen compound widely used in industry for disinfection and control of bacterial biofouling. It is also used to control taste, odor, oxidation of metal ions and color removal in other applications. Several studies have described using chlorine dioxide as an antimicrobial agent in mouth rinse applications. For example, U.S. Pat. No. 4,696,811 to Ratcliff describes a method and composition to destroy malodorous compounds; Patent No. UK 2290233A to Drayson and Butcher describes compositions for tooth whitening. Others include inventions where the oxidizing and germicidal capabilities of chlorine dioxide are activated by forming chlorine dioxide just prior to use. The main reason chlorine dioxide is generated in this way is because chlorine dioxide is an unstable gas at room temperature (boiling point of 11° C.) and is sensitive to decomposition by visible and ultraviolet light. In previous studies, the chlorine dioxide is commonly generated from the chlorite ion by acidification. It is usually provided as sodium chlorite buffered to a pH around 7 to 8 and above, and as such, referred to as stabilized chlorine dioxide (U.S. Pat. Nos. 4,689,215 and 4,837,009 to Ratcliff, Patent No. UK 2290233A to Drayson and Butcher and Patent No. WO 95/27472 to Richter). Chlorine dioxide like hydrogen peroxide above, is typically generated for the purpose of killing mouth bacteria. Where acidification of chlorite is carried out, the levels of chlorine dioxide produced are usually adequate for its germicidal purpose. But in those compositions where chlorine dioxide is stabilized as sodium chlorite at neutral or alkaline pH, formation of chlorine dioxide from chlorite ion is a relatively slow process. Accordingly, very little chlorine dioxide is available within the oral cavity as an antibacterial agent in these compositions. In contrast, in the compositions herein, chlorite ions are not used as germicidal agents. Instead they are used as effective and stable $E_h$ raising compounds, if their degradation to chlorine dioxide is avoided.

In previous inventions, chlorite ion use involves provision (rather than removal) of electrons to enable chlorite ion disproportionation and formation of the bacteriocidal compound, chlorine dioxide, a process stimulated by acid addition. The oxidation-reduction change involves change in oxidation state from +3 to +4. On the other hand, when chlorite acts as an $E_h$ raising compound as in the invention herein, its oxidation state decreases from +3 to −1. Reduction of chlorite ion is to chloride ion after going through a series of reactions involving various intermediates. What is evident from this analysis is that the chlorite ion is capable of acting as either an oxidizing or as a reducing agent depending upon the reaction conditions. Few compounds show such multi-step, and hence atypical redox buffer effects. Nonetheless, this enables them to counter or resist along with zinc ion the kinds of changes in the $E_h$ level that enable oral putrefaction to flourish and be suitable for this invention.

Using sodium chlorite as an $E_h$ raising compound rather than as a source of chlorine dioxide is very important, because chlorine dioxide at elevated levels combines with certain amino acids to produce compounds that are potentially mutagenic. Therefore, inhibition or prevention of significant chlorine dioxide formation from sodium chlorite is desirable and preferred and contra-indicated is the utilizing of sodium chlorite to generate large amounts of chlorine dioxide therefrom in order to kill enough bacteria to have significant oral effects.

A neutral pH and above is essential for chlorite ion stability and to avoid chlorine dioxide formation. Also, chloride ion is useful for additional stabilization of the sodium chlorite where there is any decrease in the pH. This is because chloride ion is produced when chlorite becomes chlorous acid and disproportionation of chlorous acid occurs $$5HClO_2 \rightarrow 4ClO_2 + Cl^- + H^+ + 2H_2O$$

This reaction is inhibited by mass action when chloride ion is provided.

Hydrogen peroxide like sodium chlorite behaves as an $E_h$ raising compound in that it can also readily react as either an oxidizing or a reducing agent. Analogous to the chlorine dioxide/chlorite/chloride system is the molecular oxygen/hydrogen peroxide/water system where chlorite ion and hydrogen peroxide. are similarly positioned as oxidation-reduction intermediates. In previous studies, the peroxide is used to generate oxygen and/or oxygen reactive species to kill the oral bacteria involved in oral disease. As found for chlorite ion, peroxide in this invention functions as an $E_h$ raising compound by removing the excess electrons of putrefaction and producing hydroxyl ions rather than giving up electrons and undergoing disproportionation as in previous patents.

The disproportionation reaction of hydrogen peroxide $$2H_2O_2 \rightarrow 2H_2O + O_2$$

is very slow under ordinary conditions but rapid in the presence of the enzymes, catalase and peroxidase, found in certain of the bacteria in the oral cavity. Once again, hydrogen peroxide is a species like chlorite ion that is thermodynamically unstable with respect to disproportionation and can function as an intermediate in oxidation-reduction reactions. Further and once again, the chloride ion inhibits the disproportionation of hydrogen peroxide but does so through inhibition of catalase.

The oxygen-oxygen single bond in hydrogen peroxide is one of the weakest covalent bonds known. It is easily broken indicating that it readily accepts electrons and as a result is able to produce hydroxyl ions. Alternatively, hydrogen peroxide is converted into the stable oxygen molecule. Previous studies have shown, using $^{18}O$ labeled hydrogen peroxide, that the oxygen produced is derived entirely from the peroxide species and not from water. This suggests that the breakdown of peroxide does not involve the breaking of the O—O bond but provides electrons to an appropriate oxidizing agent. $H_2O_2$ when used as an $E_h$ raising compound is not used as a source for molecular oxygen.

Recent studies by Douglas (U.S. Pat. Nos. 5,104,644, 5,174,990, and 5,310,546) have described oral compositions combining zinc chloride and hydrogen peroxide to treat gingivitis-periodontitis. U.S. Pat. No. 5,174,990 describes a mouth rinse containing zinc chloride and hydrogen peroxide. In these Douglas patents, it is necessary to counter the instability prior to use of the formulations described, which is caused largely because of the presence of zinc metal. To aid in stabilization of zinc, ligands that bind well to zinc such as citrate and laurylsulfate are added. However, these additions reduce the availability of free zinc, especially when these ligands are present at high ligand to zinc ratios. The mouth rinses in U.S. Pat. Nos. 5,174,990 and 5,310,546 have zinc chloride concentration ranging from 0.005% to 0.1% and a hydrogen peroxide concentration ranging from 0.25% to 0.65%. In the absence of ligands that bind zinc, zinc ion at these zinc chloride levels range in concentration between 0.002% and 0.047%. Moreover, recent studies have shown that hydrogen peroxide at the concentrations described therein are degraded by oral bacterial catalase and are not effective in vivo. Ryan and Kleinberg (1995) Archs. oral Biol., 40, 753–763. Accordingly, to compensate for the rapid breakdown of hydrogen peroxide by catalase, use of higher concentrations of hydrogen peroxide (1% or above) is necessary. At hydrogen peroxide concentrations above 3.0 to 3.5%, studies have shown that hydrogen peroxide can be harmful to the soft tissues of the oral cavity. Thus, for an oral composition containing hydrogen peroxide to be effective as a therapeutic and at the same time not harm the soft or hard tissues of the oral cavity or be harmful if swallowed, its concentration needs to be between about 1% and 3%.

In contrast, the oral compositions discovered in this invention contain sufficient chloride ions to inhibit catalase hydrolysis of the peroxide, thereby enabling peroxide to remain intact even at lower peroxide levels than 1% and for the peroxide to serve as an $E_h$ raising compound where formation of toxic products from peroxide are avoided.

Many reactions involving hydrogen peroxide in solution result in the production of free radical species, such as $HO_2$ and OH. These are effective agents for killing bacteria and such formation is a basis for the use of hydrogen peroxide as a disinfectant. Transition metal-ion catalyzed decomposition of hydrogen peroxide can readily give rise to the formation of free radicals. The destabilizing effects of zinc are avoided in this invention by using a two compartment approach where combination with zinc compound is provided just prior to use to ensure maximum availability of free zinc. The compositions described herein result in a synergism between the zinc ions, the peroxide used as an $E_h$ raising compound and the chloride ions. This two compartment system is a more desirable and effective approach than oral compositions previously described.

Methylene blue has been used as an $E_h$ raising compound. It readily accepts electrons and in this way helps prevent the electron accumulation that produces the low $E_h$ that favors oral putrefaction. In U.S. Pat. No. 5,087,451 to Wilson and Harvey, methylene blue is used to inhibit periodontitis. The beneficial effect of methylene blue alone is significantly less than achieved when used in conjunction with zinc ion as with the compositions of this invention.

SUMMARY OF THE INVENTION

The present invention is directed to oral compositions containing a zinc compound where zinc ion is freely available and at least one stabilized or stable $E_h$ raising compound distributed in an oral vehicle. In one embodiment, the oral compositions contain a zinc compound containing freely available zinc ions, hydrogen peroxide and a chloride ion containing compound. In another embodiment, the oral composition contains a zinc ion compound and an oxyhalogen compound. A further embodiment of this invention includes an oral composition containing a zinc ion compound and methylene blue.

The present invention is further directed to a method of inhibiting the formation of anionic sulfur species and thereby preventing a lowering of the $E_h$ of the oral cavity.

Specifically, the method comprises delivering into the oral cavity a therapeutically effective amount of an oral composition containing a free available zinc compound and at least one stabilized or stable $E_h$ raising compound distributed in an oral vehicle.

A further embodiment of the present invention is a method of reducing both oral malodor and gingivitis-periodontitis comprising delivering into the oral cavity a therapeutically effective amount of an oral composition containing a zinc ion compound and at least one stabilized or stable $E_h$ raising compound.

DETAILED DESCRIPTION OF THE INVENTION

The essential components and their relevant proportions in the compositions of the invention are set forth below. All patents, publications and test methods mentioned herein are incorporated by reference.

The present invention relates to an oral composition containing a zinc ion compound where a high concentration of free available zinc is provided and at least one $E_h$ raising compound distributed in an oral vehicle. A zinc ion compound as defined by the present invention is a compound containing freely available zinc ions capable of inhibiting the lowering of the oral cavity $E_h$. Important in this regard is inhibiting the breakdown of cysteine or cystine from saliva, mucosal tissues (especially the tongue) and foods by the oral bacteria. Freely available zinc ions are ions that are not bound. Zinc compounds present in the oral compositions of this invention include, for example, zinc chloride, zinc acetate, zinc lactate, zinc salicylate, zinc sulfate, and zinc nitrate. In one embodiment of the present invention, the zinc compound is zinc chloride. The concentration of zinc ion in the oral composition may range from about 0.02% to about 0.2%. In a preferred embodiment, the zinc ion concentration ranges from about 0.04% to about 0.12%.

A stabilized $E_h$ raising compound as defined herein is a compound capable of directly or indirectly raising the $E_h$ of the oral cavity. Examples of $E_h$ raising compounds include, for example, hydrogen peroxide, oxyhalogen species such as sodium chlorite and biologically compatible oxidation-reduction (redox) buffers such as methylene blue. Additional examples of $E_h$ raising compounds include common fermentable sugars such as glucose, galactose, fructose, maltose, lactose and sucrose. These compounds when metabolized by oral bacteria and in particular, the oral streptococci, in the presence of oxygen produce, inter alia, hydrogen peroxide.

The concentration of the $E_h$ raising compound in the oral compounds of this invention may range from about 0.1% to about 3.0% by weight of the composition. In a preferred embodiment, the concentration of the $E_h$ raising compound is about 0.1% to about 1.0%. When the $E_h$ raising compound is hydrogen peroxide or a fermentable sugar, a chloride ion containing compound is added to the oral composition in an amount sufficient to inhibit catalase in the oral cavity from breaking down the hydrogen peroxide. The chloride ion containing compound is a compound capable of inhibiting the catalase activity in the oral cavity. Suitable chloride ion containing compounds include alkali metal chloride salts and alkali earth metal chloride salts such as, for example, NaCl and $CaCl_2$. Generally, the concentration of the chloride ion containing compound in the oral composition ranges from about 0.5% to about 2.5% by weight of the composition. Since some oral microbiota produce hydrogen peroxide in the presence of fermentable sugars, chloride ions are also added to make it more effective.

In one embodiment of this invention the zinc compound is zinc chloride, the $E_h$ raising compound is hydrogen peroxide and the chloride ion containing compound is sodium chloride. In another embodiment of this invention, the oral composition contains zinc chloride, a fermentable sugar and sodium chloride. In a further embodiment of this invention, the oral composition contains zinc chloride and the oxyhalogen species sodium chlorite and with or without sodium chloride. A further embodiment of the present invention consists of oral compositions containing zinc chloride and methylene blue with or without sodium chloride.

We have discovered that the pH of the oral compositions of the present invention is specific to the zinc compound and $E_h$ raising compound combination used. When the $E_h$ raising compound is hydrogen peroxide, the preferred pH of the oral compositions generally ranges from about 3.0 to about 6.0. In one embodiment, the pH ranges from about 3.5 to about 4.5. An acidic pH has two desirable effects. First, an acidic pH ensures availability of the zinc ion since zinc ion above a pH of about 6.0 combines with hydroxyl ions in solution to form poorly soluble zinc hydroxide, thereby making zinc ion unavailable. Second an acidic pH converts sulfur anions to the acidic forms which result in a higher $E_h$. In the case of hydrogen sulfide, because hydrogen sulfide is volatile, its formation serves as an effective means of getting rid of electrons carried by sulfide anion that are particularly conducive to lowering the $E_h$. Third, catalase degradation of hydrogen peroxide is inhibited at an acidic pH. An acidic pH and the presence of chloride ion, ensures that the hydrogen peroxide in the composition is not degraded with storage and hence retains its effectiveness.

On the other hand, when the $E_h$ raising compound is the oxychloride, sodium chlorite, a pH between about 3.0 and 6.0 is unsuitable for the stability of sodium chlorite during its storage. At acidic pH, unstable and less desirable chlorine dioxide is produced. To be of use for the purpose of this invention, the pH of the sodium chlorite during storage needs to be between about 7.0 and about 8.5 where it is most stable. The instability of zinc ion at a pH of 6.0 and above and the instability of chlorite at a pH of about 6.0 and below necessitates the two being kept separate in a two compartment system until ready for use. When brought into contact with each other immediately before mixture use, the preferred pH is between about 5.5 and about 6.0. Addition of chloride ion as sodium chloride and/or as part of zinc chloride, provides stability along with synergistic activity. The pH of the oral compositions described herein can be controlled with acids such as hydrochloric and benzoic and with base such as sodium hydroxide.

In addition to the zinc-peroxide-chloride ion composition, the zinc-oxyhalogen composition, and the zinc-methylene blue composition, the oral compositions described in accordance with the present invention may contain any conventional ingredient for the particular oral composition. For example, liquid mouthwashes may contain a solvent such as distilled or deionized water, and ethanol; a sweetening agent such as sorbitol, mannitol, xylitol, saccharin and aspartame; and a flavoring agent such as peppermint oil, and spearmint oil. (See U.S. Pat. Nos. 4,226,851; 4,209,754; 4,289,755; and 5,104,644). Because of the formulation difficulties associated with zinc ion instability at about pH 6.0 and above resulting from the forming of poorly soluble zinc hydroxide and the instabilities of many $E_h$ raising compounds such as sodium chlorite and hydrogen peroxide, two compartment systems where the zinc ion compound and the $E_h$ raising compound are in respective compartments but can be mixed immediately prior to use are preferred. An example of a two compartment composition for zinc chloride and sodium chlorite is shown in Table 2.

Dentifrices may contain, for example, a conventional abrasive such as calcium pyrophosphate, aluminum hydroxide, resins, insoluble alkali metal metaphosphates and silica in a standard amount of 20–60% wt.; a binder such as hydroxyethyl cellulose, xanthin gum and sodium carboxymethylcellulose in a standard amount of 0.5–5.0% wt.; a foaming agent such as sodium lauryl sulfate, sodium coconut monoglyceride sulfonate and sodium-N-methyl-N-palmitoyl tauride in a standard amount of 0.5–3.0% wt.; a flavoring agent; a sweetening agent; an antiseptic agent and any other ingredient required for the particular formulation. (See U.S. Pat. No. 5,372,802). Two compartment delivery systems are preferred. Tables and powders may contain, for example, a vehicle such as lactose or mannitol; a binder such as corn starch or carboxymethyl cellulose; and a disintegrator, once more in two compartment delivery systems.

The present invention is also directed to a method of inhibiting the formation of sulfur containing anions in the oral cavity and preventing a lowering of the $E_h$ of the oral cavity by delivering into the oral cavity a therapeutically effective amount of an oral composition containing, a zinc ion compound and at least one $E_h$ raising compound distributed in an oral vehicle. As defined by the present invention, sulfur containing anions include for example, sulfide ($S^-$), hydrogen sulfide anion ($HS^-$) and methyl mercaptan anion ($CH_3S^-$). A therapeutically effective amount of oral composition is an amount sufficient to inhibit the formation of sulfur containing anions and prevent a lowering of the $E_h$ of the oral cavity. For example, a therapeutically effective amount of the oral composition in a dentifrice or mouth rinse may range from approximately 0.5% to approximately 5% by weight and preferably 2% to 3% by weight of the composition.

Acceptable oral vehicles include, for example, any conventional oral delivery system, such as dental care products, food products and chewing gum. Examples of dental care products include for example, dentifrices, topical solutions or pastes, mouthwashes in the form of liquids, powders, gels or tablets, and dental flosses. Examples of food products which contain the oral compositions described herein include, for example, lozenges and confectioneries.

The present invention is further directed to a method of reducing oral malodor, gingivitis and periodontitis by delivering into the oral cavity a therapeutically effective amount of an oral composition containing a zinc ion compound and at least one $E_h$ raising compound distributed in an acceptable oral vehicle. As defined by the present invention, a therapeutically effective amount of an oral composition is an amount sufficient to raise the $E_h$ of the oral cavity to normal levels and prevent or reduce oral malodor, gingivitis and periodontitis. For example, a therapeutically effective amount of an oral composition is an amount sufficient to reduce or prevent the formation of malodorous compounds such as hydrogen sulfide and the growth of harmful Gram-negative anaerobic bacteria which may cause gingivitis and periodontitis. A therapeutically effective amount of the oral composition in a dentifrice or mouthwash may range from approximately 0.5% to approximately 5% by weight and preferably about 2% to about 3% by weight of the composition.

The present invention further provides an article of manufacture comprising a packaging material and the oral compositions described herein contained within said packaging material, wherein said oral composition is effective in preventing and/or reducing any decrease in the $E_h$, oral putrefaction and development of oral malodor, gingivitis and periodontitis and wherein said packaging material contains a label that indicates that said oral composition is effective in raising the $E_h$, and reducing oral putrefaction, oral malodor, gingivitis and periodontitis. The packaging material used to contain the oral compositions can comprise glass, plastic, metal or any other suitably inert material. For example, a dentifrice containing the oral composition of the present invention may be contained in a collapsible tube, typically aluminum, lined lead or plastic or a squeeze, pump or pressurized dispenser for measuring out the contents or in a tearable sachet.

In order to further illustrate the present invention, the experiments described in the following examples were carried out. It should be understood that the invention is not limited to the specific examples or the details described therein. The results obtained from the experiments described in the examples are shown in the accompanying table and figures.

EXAMPLE I

This Example demonstrates the ability of salivary supernatant to lower the $E_h$ and the ability of glucose to act as an $E_h$ raising compound to raise the $E_h$ in the salivary sediment system model developed by Kleinberg (1967 and 1970) *Archs. oral Biol.*, 12:1457–1473; *Advances oral Biol.* (Volume 4) New York, N.Y. Academic Press pp. 49–50 (see FIG. 2). This model utilizes the mixed oral bacteria collected in the salivary sediment obtained from whole saliva by centrifugation. Extensive studies have shown that this system behaves metabolically like dental plaque (Singer et al. (1983) *Archs. oral Biol.* 28:29–35; Wijeyeweera and Kleinberg (1989 a and b) *Archs. oral Biol.* 34:43–64; Salako and Kleinberg (1992) *Archs. oral Biol.* 37:821–829; Ryan and Kleinberg (1995) *Archs. oral Biol.* 40:743–752). This model is recognized in the art as an effective proxy to study the microbial metabolic and related biochemical processes of the oral cavity. The ability of the different amino acids available from salivary peptides and proteins to lower the $E_h$ in the salivary sediment system is shown in Table 1.

To collect salivary sediment and salivary supernatant for the assay, saliva stimulated by chewing paraffin wax was expectorated into test-tubes chilled in cracked ice. The donors had not brushed their teeth for 24 hours prior to collection. The donors were also instructed to fast for at least 12 hours to provide stimulated whole saliva which contains a minimal level of endogenous carbohydrate. (Kleinberg and Jenkins (1964) *Archs. oral Biol.*, 9:493–516). Following collection, the saliva was centrifuged at 1740×g for 15 minutes and the supernatant was subsequently removed by pipette and kept on ice until the assay was run. Next, the sediment was washed three times with ice cold distilled water to remove any residual salivary supernatant. The washed salivary sediment was chilled in crushed ice until the assay was run. Prior to incubating the samples and running the assay, the washed salivary sediment was re-suspended in distilled water to a final concentration of 50 per cent (V/V).

To assay the ability of various amino acids and salivary supernatant to produce a lowering of the $E_h$, incubation tubes were prepared containing the following: 16.7% (V/V) salivary sediment, 60 mM phosphate buffer and either 33.3% (V/V) salivary supernatant or 3 mM amino acid. A control tube contained sediment and water. All incubation mixture preparations were done with the test-tubes chilled in cracked ice until they were transferred to a water bath for incubation at 37° C. for 24 hours. Measurements were taken at the following time intervals: 0 and 30 min and 1, 2, 3, 8 and 24 hours.

The oxidation-reduction potential ($E_h$) was determined in each incubation mixture using a platinum electrode and a potassium chloride salt bridge leading to a calomel reference electrode connected to a pH meter used as a millivoltmeter. All $E_h$ measurements were related to the standard hydrogen electrode by adding the value 242 millivolts to the reading made with this electrometric system. The lowest $E_h$ reached with each amino acid is shown in Table 1. The corresponding lowest $E_h$ levels reached with salivary supernatant and the water control are shown at the bottom of the table. The $E_h$ with supernatant falls to the lowest $E_h$ and is only matched by the amino acid, cystine. Of the various amino acids tested, the sulfur containing amino acids—cystine, cysteine and methionine (Group C) showed the lowest $E_h$; arginine, glutamic, ornithine and tyrosine (Group B) showed next lowest; and the remainder (Group A) showed the highest $E_h$ levels. Fractionation experiments of salivary supernatant identified small peptides with cystine as the constituent mainly responsible for the $E_h$ lowering activity of salivary supernatant.

EXAMPLE II

Figure 1:
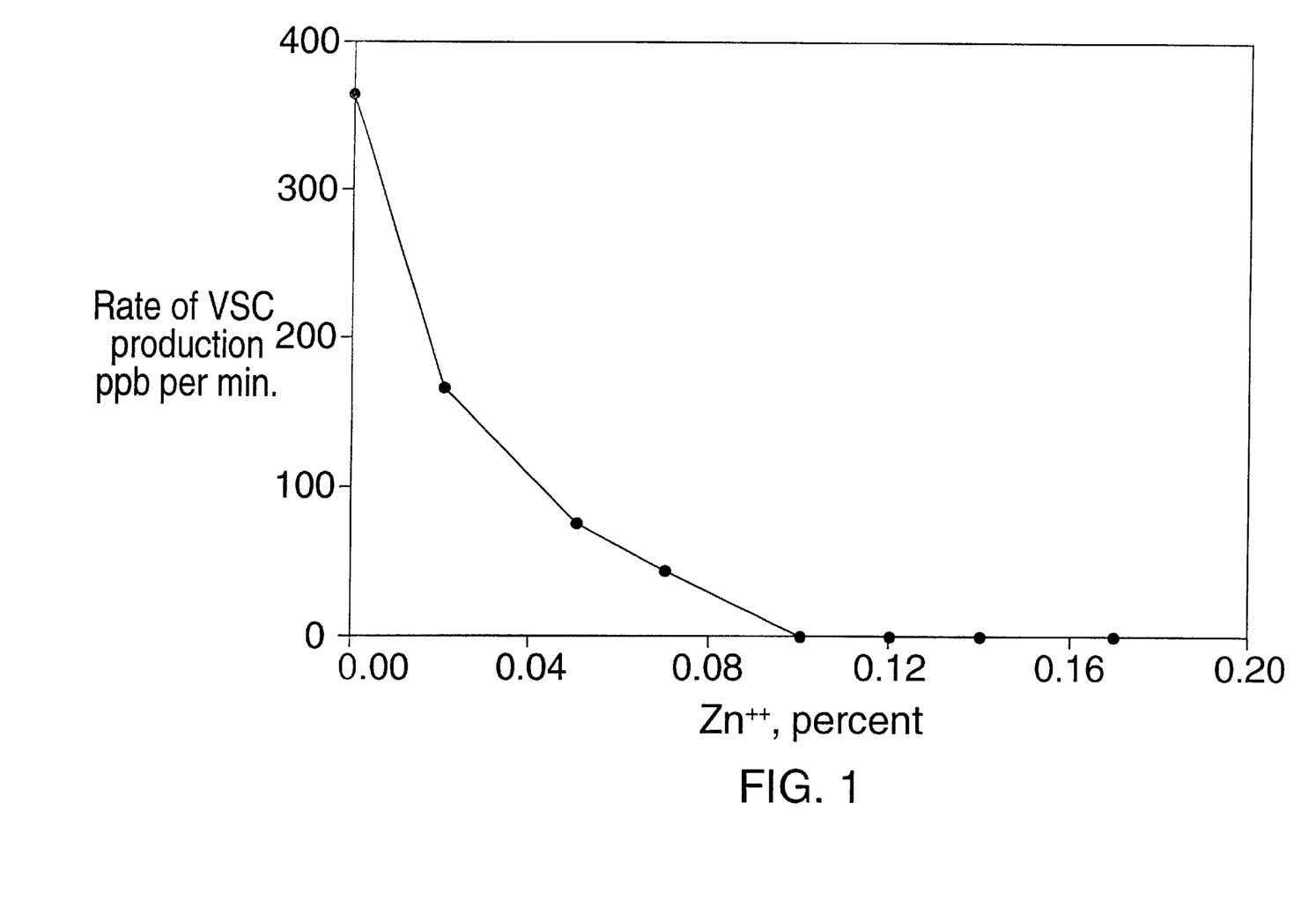
FIG. 1 shows the relation between zinc ion concentration and the rate at which the oral bacteria are able to produce volatile sulfur compounds and associated sulfur anions from cysteine. Inhibition is exponential and occurs maximally once the zinc ion concentration reaches about 0.2%.
Figure 2:
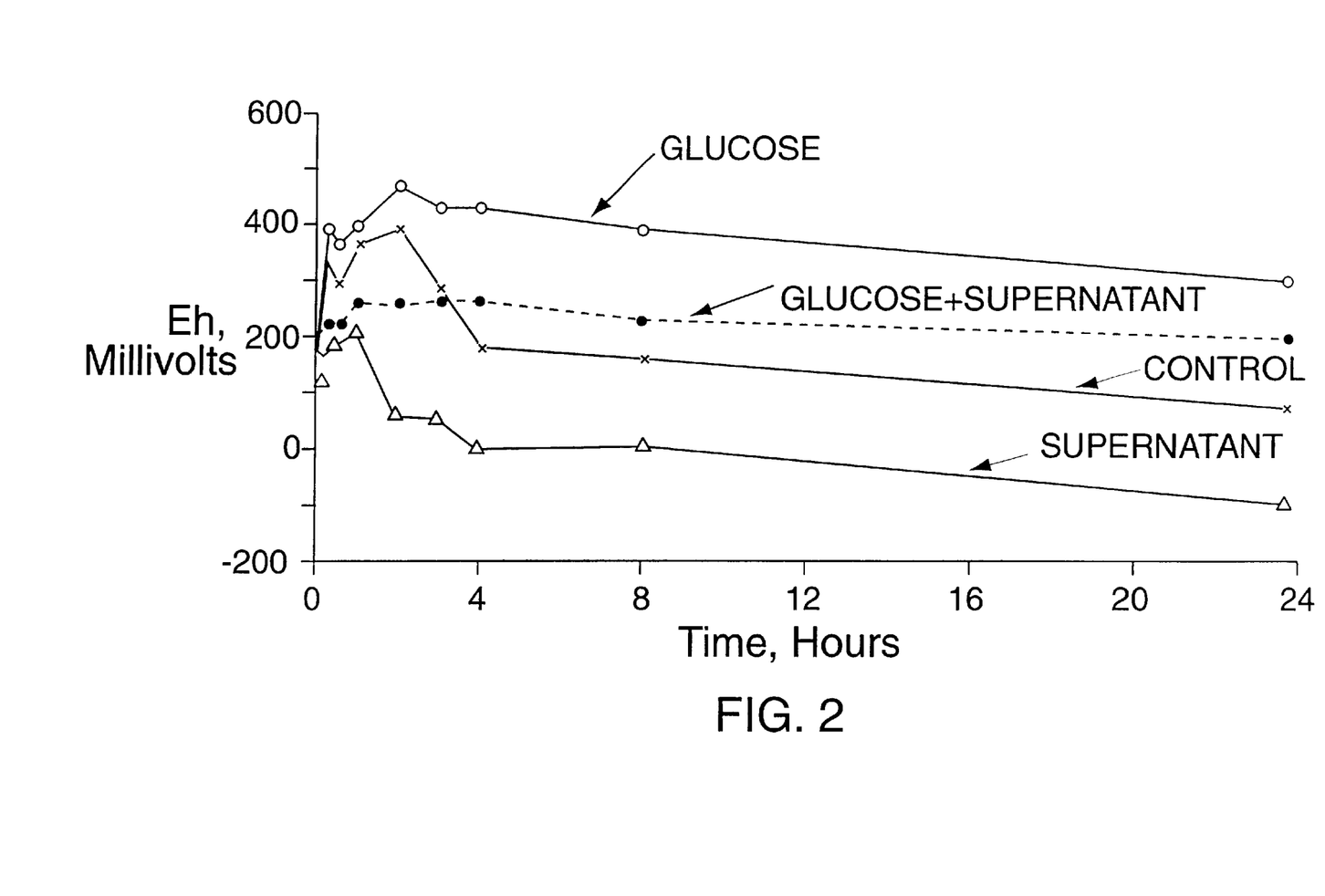
FIG. 2 shows the changes in the $E_h$ during an incubation of mixed oral bacteria and (i) salivary supernatant (ii) glucose (iii) salivary supernatant and glucose and (iv) a water control.

A similar type of in vitro experiment as in Example I was carried out to assay the ability of (i) zinc chloride, (ii) hydrogen peroxide, and (iii) zinc chloride and hydrogen peroxide, to prevent a fall in the $E_h$ of the oral cavity. Incubation tubes were prepared containing 16.7% sediment, 60 mM phosphate buffer, and (i) zinc chloride at a concentration of 6.0 mM (0.08%), (ii) hydrogen peroxide at a concentration of 0.5%, or (iii) zinc chloride at a concentration of 6.0 mM and hydrogen peroxide at a concentration of 0.5%. A tube was prepared containing salivary sediment and salivary supernatant only (water control). FIG. 2 shows the $E_h$ of the mixtures during incubation at 37° C. over a 24-hour time period.

Figure 3:
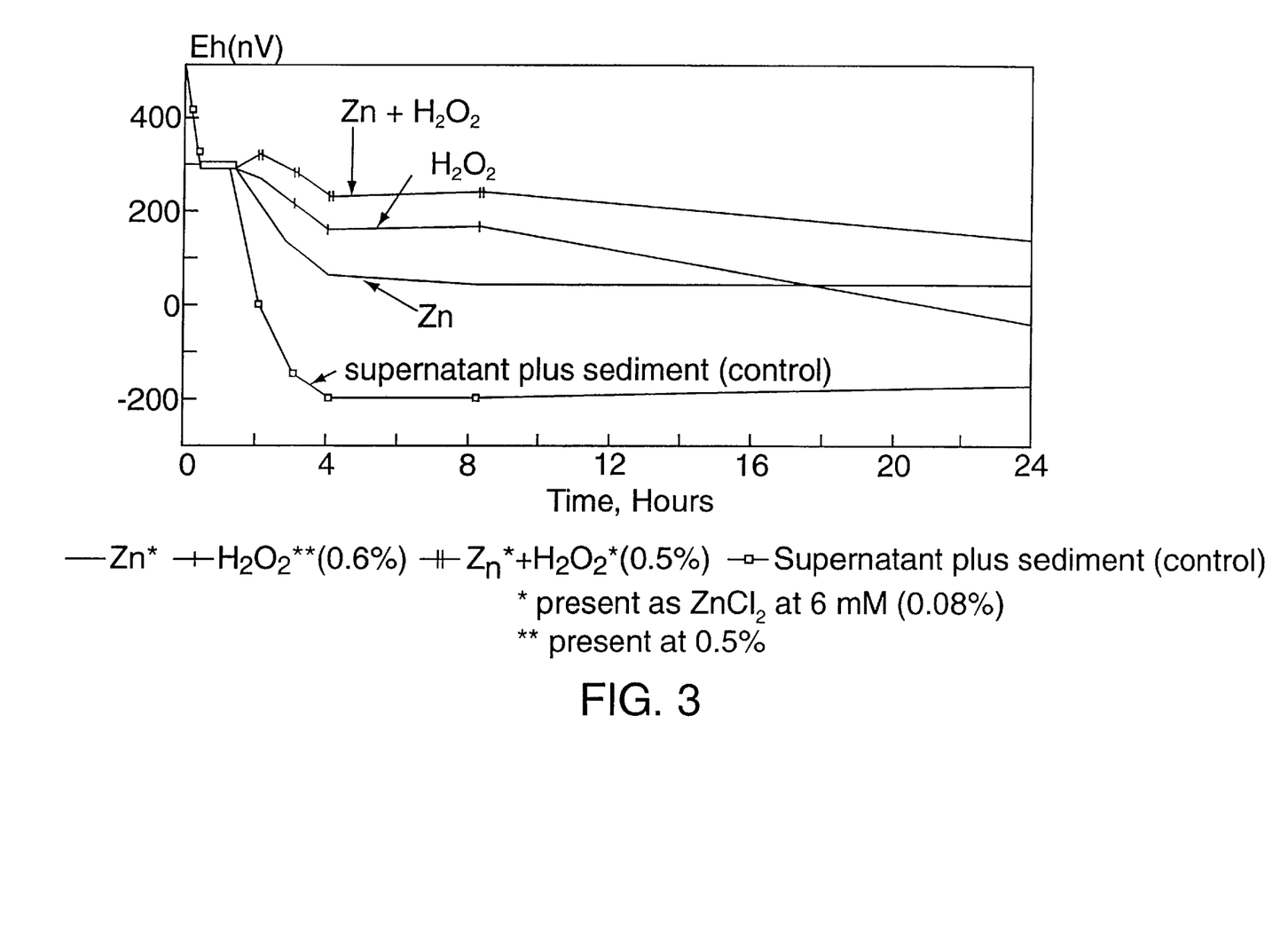
FIG. 3 shows the changes in $E_h$ during an incubation of mixed oral bacteria and salivary supernatant with (i) zinc chloride (ii) hydrogen peroxide and (iii) zinc chloride ion plus hydrogen peroxide. A control incubation containing mixed oral bacteria with salivary supernatant is also shown. Hydrogen peroxide by itself loses some of its ability to inhibit the $E_h$ lowering due to hydrogen peroxide degradation by bacterial catalase during the incubation.

As shown in FIG. 3, zinc chloride and hydrogen peroxide alone, or in combination, significantly raised the $E_h$ of the incubation mixture compared to the salivary supernatant plus salivary sediment control. The control incubation mixture containing only sediment and supernatant showed a rapid and extensive lowering of the $E_h$. The incubation mixtures with zinc chloride alone and hydrogen peroxide alone, showed some decrease in the $E_h$. Hydrogen peroxide alone progressively lost some of its $E_h$ reducing ability as there was no chloride present unlike in zinc chloride to inhibit its degradation by catalase. When zinc chloride and hydrogen peroxide were combined in the incubation, only a slight decrease in the $E_h$ occurred. The results in this example demonstrated the ability of a composition containing zinc chloride and hydrogen peroxide to reduce the decrease in the $E_h$, and thereby reduce the oral putrefaction that is conducive to the development of oral malodor, gingivitis and periodontitis.

EXAMPLE III

This example shows the ability of the zinc ion-peroxide-chloride ion compositions of the present invention to retard or reduce the $E_h$ lowering ability of the oral bacteria and their ability to produce malodor. As shown in Example II, hydrogen peroxide can have an inhibitory effect on odor production by the mixed bacteria that comprise the microflora of the salivary sediment system. However, it will be difficult for peroxide to persist in this system or in dento-gingival or tongue plaque in situ because their microfloras contain bacteria that have exceptionally high catalase and peroxidase activities. (Ryan and Kleinberg (1995) *Archs. oral Biol.* 40:743–752). Consequently, for peroxide to be effective in the mouth, it is necessary to inhibit this catalase activity. Otherwise, peroxide levels well over 1% would be necessary to reduce the oral malodor and this concentration can be harmful to the oral soft tissues. An agent presently documented to be inhibitory of catalase activity is chloride ion.

This assay examined the effects of rinsing with a combination of $ZnCl_2$, $H_2O_2$ and NaCl on the $E_h$ and odor producing activity of the oral bacteria The oral rinse consisted of $ZnCl_2$ at 6 mM (0.08%), NaCl at 500 mM (2.9%) and $H_2O_2$ at 1%.

The oral rinse was tested for its effects on the $E_h$ lowering and oral malodor forming activity of the oral bacteria. The oral malodor formation was assessed organoleptically, measuring VSC using a Halimeter (Model RH-17A Interscan Portable Analyzer) and measuring the formation of indole/skatole using Kovac's method. Gadebusch H. H. and Gabriel S. (1956)." Modified Stable Kovac's Reagent for the Detection of Indole", *Amer. J. Clin. Path.* 26 1373–1375. The organoleptic measurements were done by having a trained individual smell the odor produced and rate the odor on a scale of 0–4, with zero indicating no malodor and four indicating strong malodor. In the Kovac method, Kovac's Reagent (P-Dimethylaminobenzaldehyde dissolved in amyl alcohol and acidified with HCl) was added to each assay sample and the bluish/red color was measured at 567 nm in a spectrophotometer.

Experiments were run on subjects who had fasted and carried out no oral hygiene for the last 12 h. Testing was started between approximately 9 a.m. and 10 a.m. For the baseline sample, the subject cleared saliva from the mouth by gentle expectoration and rested for a period of 2 minutes to allow fresh saliva to collect. This saliva was then spit into a test tube chilled in cracked ice. If the collected saliva was less than 750 ml a further 2 minute period was used for collection. Following the baseline collection, the subject rinsed his/her mouth with 5 ml of the test solution for 20 seconds and a saliva sample was collected as above. The collection once more was for a 2 minute period. Saliva samples were also collected at different times up to four hours following the rinse. 750 ml of each saliva sample was immediately incubated in a 37° C. water bath and the $E_h$, odor index, and volatile sulfur compounds (VSC) in each sample were determined at 0, 15 and 30 minutes and at 1, 2, 3, 4, 8 and 24 h; these values were averaged to give a mean value assay of each parameter in each sample. Subjects were tested on 3 different days. Day one was without the use of a rinse, day two with a water rinse and day three with a zinc-peroxide-chloride ion rinse.

Figure 4:
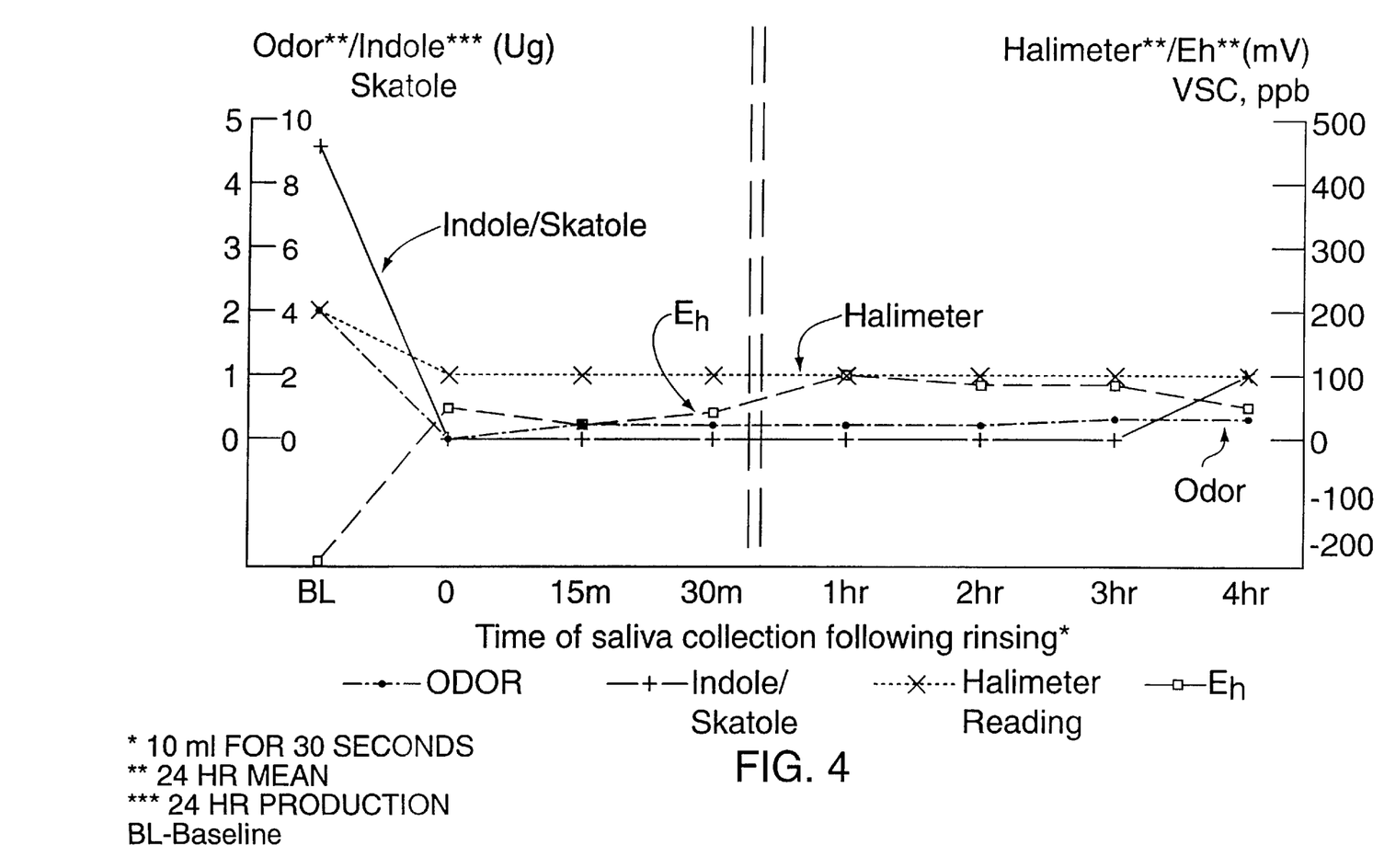
FIG. 4 shows the mean $E_h$, odor index, volatile sulfur compound (VSC) level and the level of indole/skatole produced in samples taken at intervals in a 4 hour period after rinsing with a mouth rinse containing zinc chloride (0.08%), hydrogen peroxide (1%) and NaCl (2.9%). VSC levels are measured with an instrument called the Halimeter.

FIG. 4 shows the results after the zinc-hydrogen peroxide-chloride ion rinsing. As shown by this figure, the zinc-hydrogen peroxide-chloride ion composition of the present invention favored a more positive $E_h$ level and its effect on odor was dramatic. Odor production determined organoleptically and by indole/skatole formation were almost totally retarded and the production of VSC was significantly reduced. No changes from base-line (BL) were seen when water was the rinsing solution or no rinsing was done. The oral composition of the present invention affected the $E_h$ positively and suppressed odor parameters even after 4 hours following the rinse. Only indole/skatole formation began to return after 4 hours. These results demonstrate the ability of the oral compositions described herein to reduce oral malodor by preventing the ability of the oral bacteria to reduce the $E_h$ of the oral cavity.

EXAMPLE IV

Figure 5:
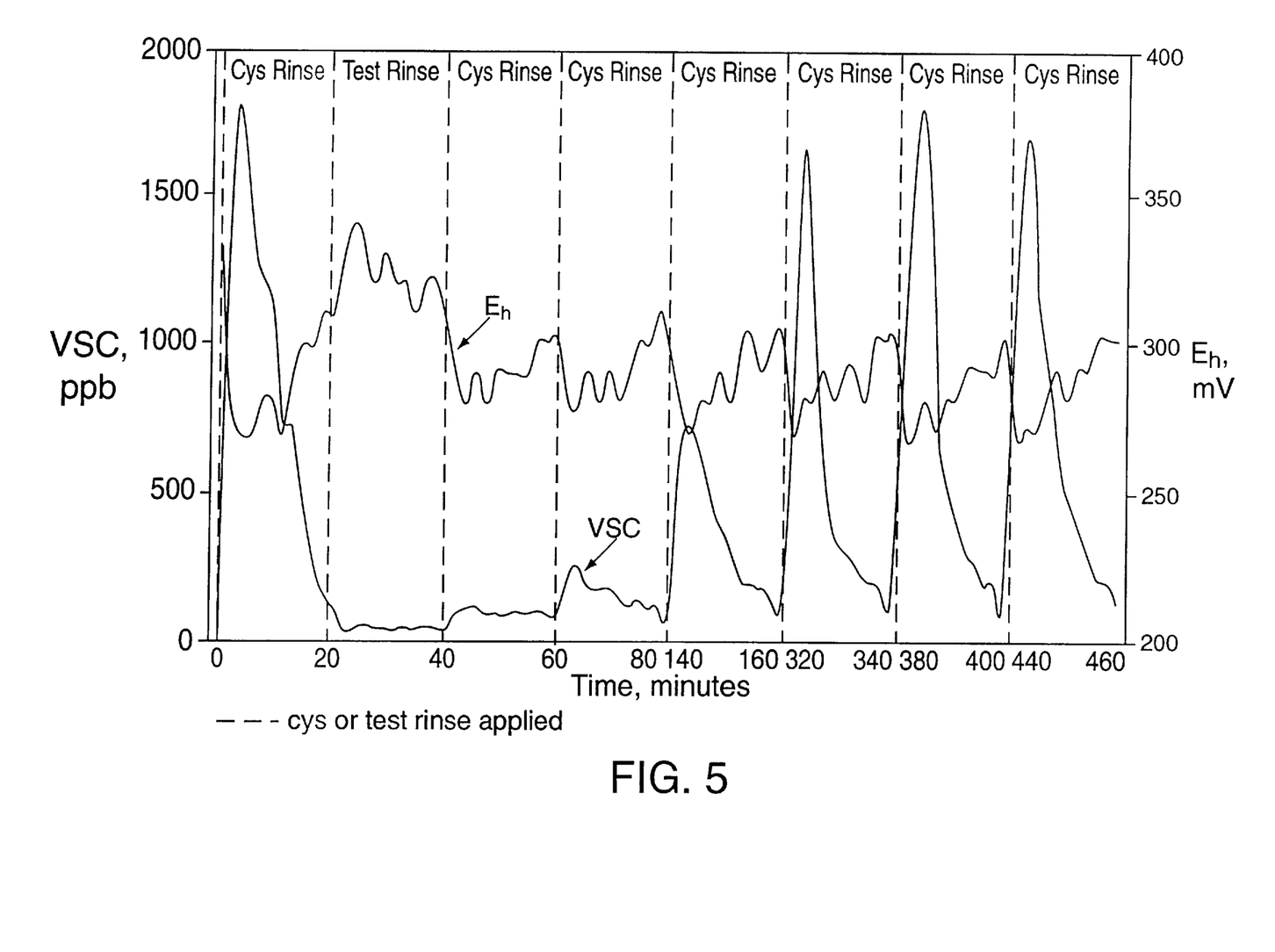
FIG. 5 shows the concentration of volatile sulfur compounds and the $E_h$ in vivo following rinsing with cysteine (VSC and $E_h$ responses) before and after a mouth rinse containing zinc chloride at 6 mM (0.08%).

The ability of a zinc chloride rinse solution to reduce or prevent the formation of volatile sulfur compounds (VSC) in vivo following successive challenges with a cysteine rinse was studied in this Example. The rinse solution consisted of zinc chloride at 6 mM (0.08%). Experiments were run on subjects who had fasted and carried out no oral hygiene for at least 12 hours. The subject rinsed his/her mouth with 5 ml of a 6 mM cysteine solution for 30 seconds to stimulate substantial VSC production by the oral bacteria This test is analogous to the use of glucose as a challenge substrate to determine the glycolytic activity of dental plaque bacteria (Stephan, R. M. 1944. *J. dent. Res.* 23, 257) or ingestion of a fixed amount of glucose as a challenge in assaying for diabetes activity. Before and following the rinse, a Halimeter instrument was used to measure the volatile sulfur compounds (VSC) produced. Simultaneously, a platinum electrode was placed on the posterior dorsum surface of the tongue, just anterior to the circumvallate papillae to measure the $E_h$. After 20 minutes, the subject rinsed his/her mouth with 5 ml of the zinc chloride solution for 30 seconds. Again, the VSC of the subject's mouth air and the $E_h$ were measured. The subject then rinsed successively with the 6 mM cysteine solution at 40, 60, 140, 320 and 380 minutes and the VSC and $E_h$ of the subject's oral cavity were re-measured each time (see FIG. 5) using the Halimeter and the platinum electrode. As shown in FIG. 5, the zinc chloride rinse reduced the ability of the oral bacteria to produce the VSC response to cysteine rinsing and retarded the production of the VSC response to subsequent cysteine rinses for about 5 hours thereafter. The same figure also shows the $E_h$ response that occurs co-incident with the VSC response after cysteine challenging. The $E_h$ was raised to a small degree during rinsing with the zinc chloride solution. Clearance of the cysteine by saliva and rapid utilization of the cysteine by the oral bacteria facilitates the removal of the cysteine and the returning of the VSC and to their respective baselines during each cysteine challenge episode. As demonstrated by this in vivo assay, zinc chloride is a compound that is able to reduce the ability of the oral bacteria to generate volatile sulfur compounds. This contributes to reduced oral putrefaction activity and in turn reduced oral malodor production and gingivitis-periodontitis.

EXAMPLE V

Figure 6:
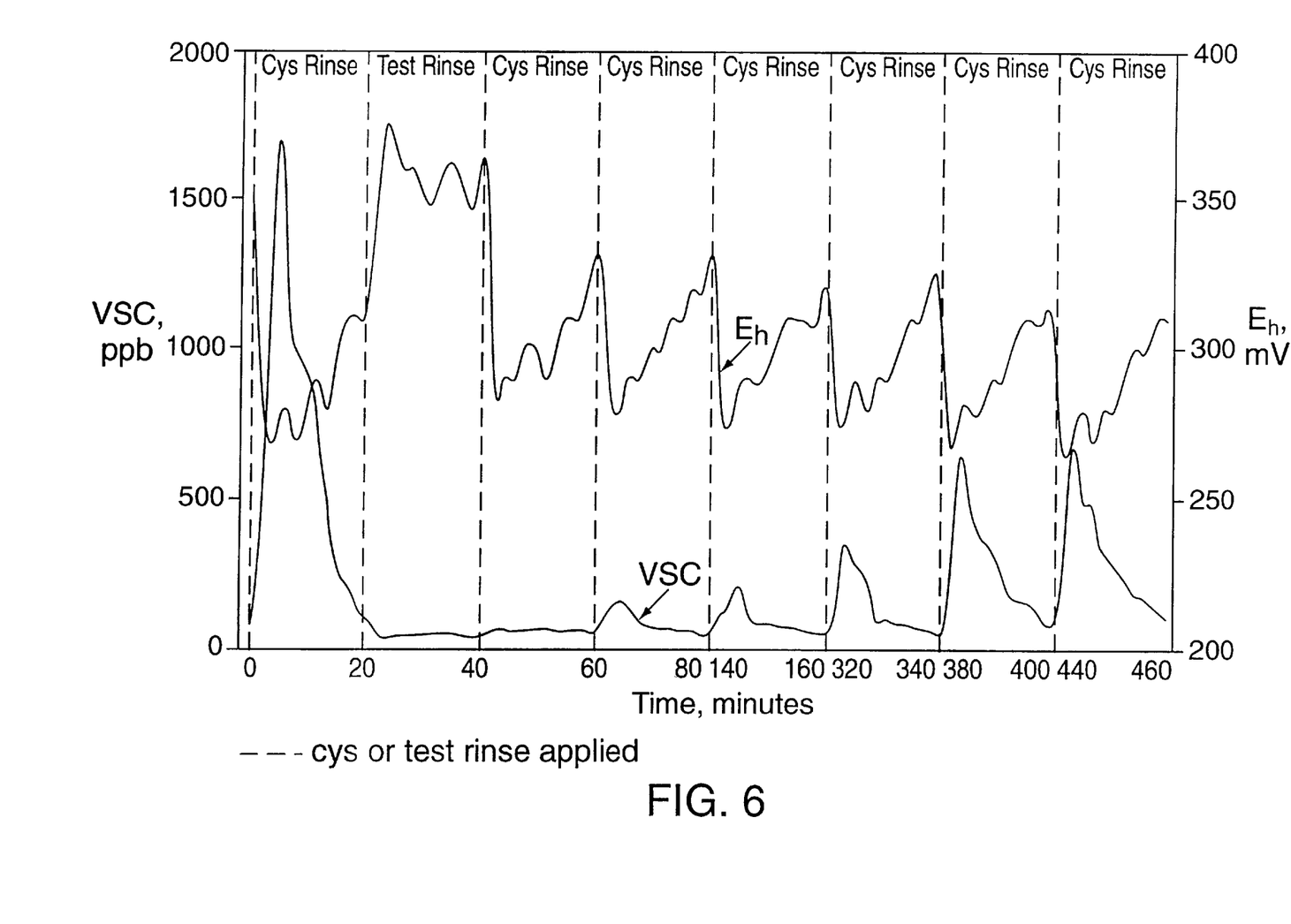
FIG. 6 shows the concentration of volatile sulfur compounds and the $E_h$ in vivo following rinsing with cysteine (VSC and $E_h$ responses) before and after a mouth rinse containing zinc chloride at 6 mM (0.08%), hydrogen peroxide at 1% and sodium chloride at 500 mM (2.9%).

The ability of a zinc-hydrogen peroxide-salt composition to reduce or prevent the formation of VSC in vivo following successive challenges with a cysteine rinse was studied in this Example in the same way as in Example IV. The oral rinse consisted of zinc chloride at 6 mM (0.08%), hydrogen peroxide at 1% and sodium chloride at 500 mM (2.9%). As before, 5 ml of the zinc/peroxide/chloride ion composition of this invention was applied as a rinse for 30 seconds. VSC and $E_h$ measurements were also carried out as before and the results are shown in FIG. 6. The zinc-peroxide-chloride ion rinse of this invention showed greater inhibition of VSC production and for a longer time than in Example IV where the zinc chloride was tested without peroxide and chloride ion. The $E_h$ rose strongly and more with the zinc chloride-peroxide-sodium chloride composition following its application than did zinc chloride alone in Examplae IV and the subsequent $E_h$ responses were initially inhibited and return to the baseline response was delayed. This Example shows that the oral composition of the present invention is able to significantly inhibit VSC production from cysteine and its ability to lower the $E_h$, and has the ability to raise the $E_h$ when introduced in vivo.

EXAMPLE VI

Figure 7:
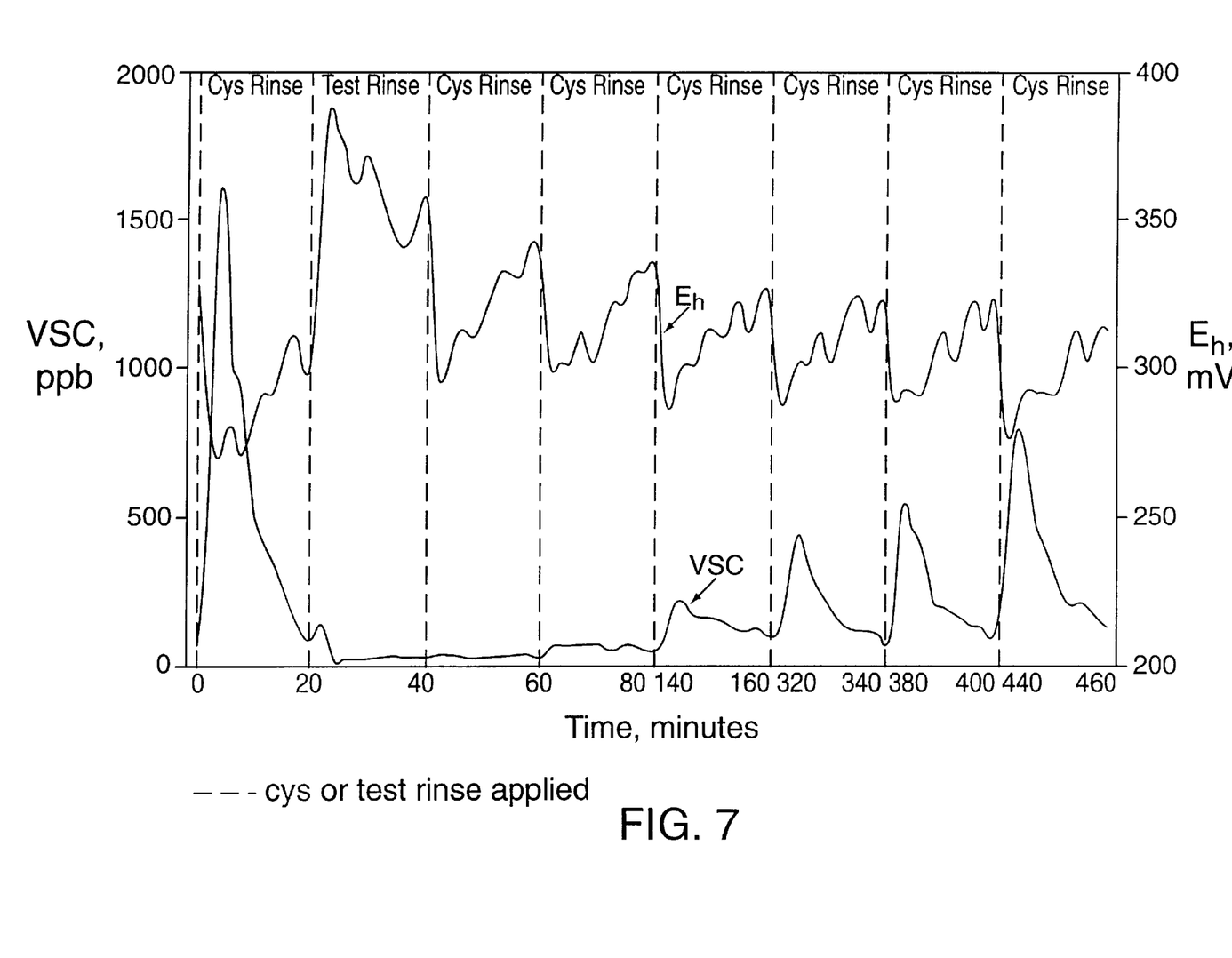
FIG. 7 shows the concentration of volatile sulfur compounds and the $E_h$ in vivo following rinsing with cysteine (VSC and $E_h$ responses) before and after a mouth rinse containing zinc chloride at 6 mM (0.08%) and sodium chlorite at 0.5%.

The ability of a zinc-chloride-sodium chlorite composition to reduce or prevent the formation of VSC in vivo following successive challenges with a cysteine rinse was studied in this Example in the same way as in Examples IV and V. The oral rinse consisted of zinc chloride at 6 mM (0.08%) and sodium chlorite at 0.5%. As before, 5 ml of the zinc/peroxide/chloride ion composition of this invention was applied as a rinse for 30 seconds. VSC and $E_h$ measurements were also carried out as before and the results are shown in FIG. 7. The zinc-chloride-sodium chlorite rinse of this invention showed as in Example V, greater inhibition of VSC production and for a longer time than in Example IV where the zinc chloride was tested without sodium chlorite. The $E_h$ rose strongly and more with the zinc chloride-sodium chlorite composition following its application than did zinc chloride alone in Example IV; the subsequent $E_h$ responses were initially inhibited and return to the baseline response was delayed. This Example shows that the oral composition of the present invention is able to significantly inhibit VSC production from cysteine and its ability to lower the ($E_h$, and has the ability to raise the $E_h$ upon introduction into the oral cavity.

EXAMPLE VII

Figure 8:
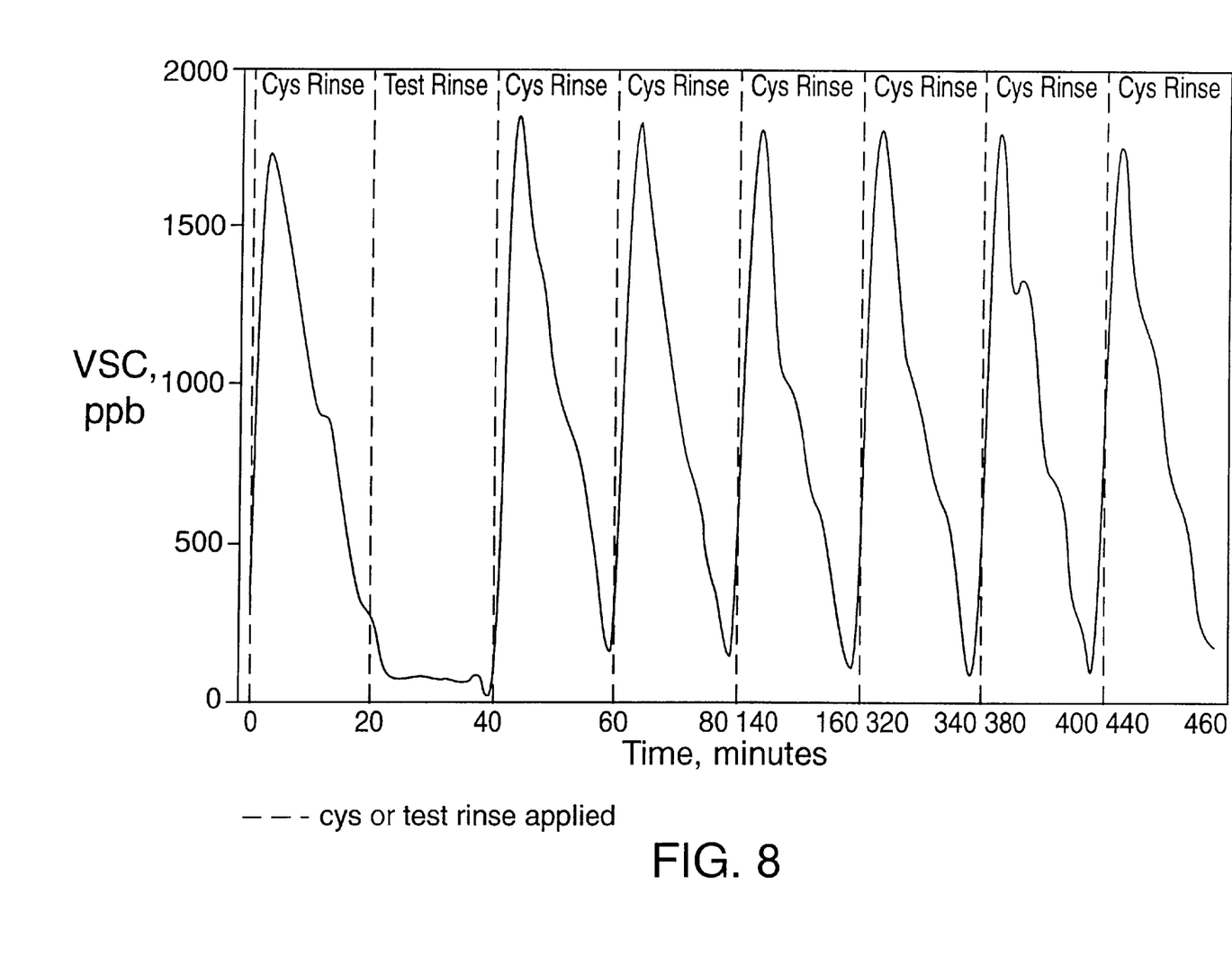
FIG. 8 shows the concentration of volatile sulfur compounds in vivo following rinsing with cysteine (VSC and $E_h$ responses) before and after a mouth rinse containing sodium chlorite at 0.1%.
Figure 9:
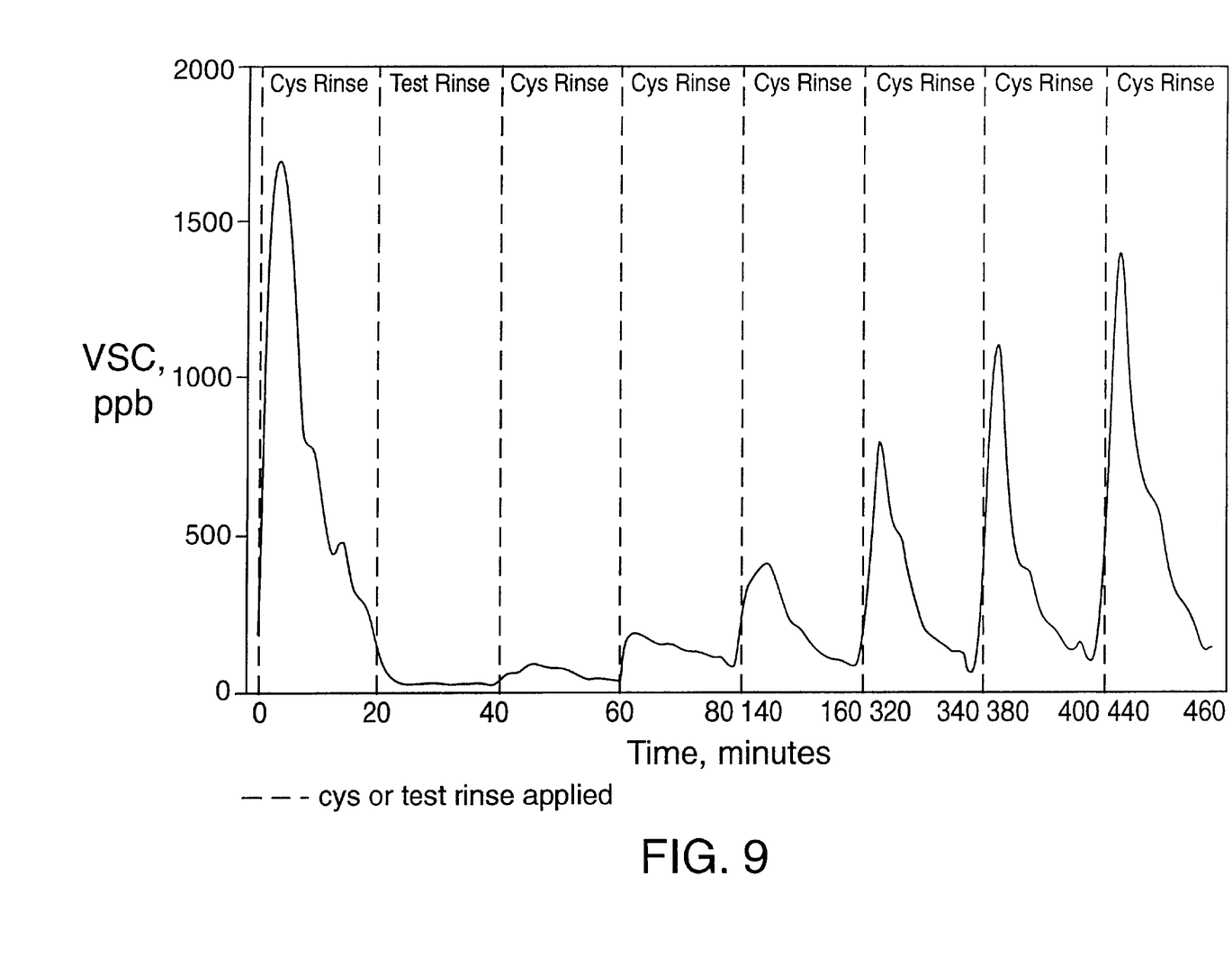
FIG. 9 shows the concentration of volatile sulfur compounds in vivo following rinsing with cysteine (VSC and $E_h$ responses) before and after a mouth rinse containing sodium chlorite at 0.1% and zinc chloride at 6 mM (0.08%).

The abilities of 0.1% sodium chlorite rinse solutions, one without and one with zinc chloride at 6 mM (0.08%) were compared in this Example for their abilities to reduce or prevent the formation of VSC in vivo following successive challenges with a cysteine rinse as before. The oral rinse consisted of application of 5 ml for 30 seconds of either an 0.1% sodium chlorite solution or an 0.1% sodium chlorite solution to which zinc chloride at 0.08% had been added. VSC and $E_h$ measurements were carried out as before and the results are shown in FIGS. 8 and 9. The sodium chlorite showed no inhibition of VSC production (FIG. 8) whereas the zinc chloride-sodium chlorite combination was inhibitory and more so than observed for zinc chloride alone (FIG. 5) in Example IV. This Example shows that combining zinc chloride and sodium chlorite can produce a greater effect than expected from simple addition of their individual effects.

We claim:

1. An oral composition comprising a first component containing zinc chloride, which yields freely available zinc ions, in a first vehicle suitable for introduction to the oral cavity and a second component containing sodium chlorite in a second vehicle suitable for introduction to the oral cavity, wherein said first and second components are stored separately and mixed prior to using the oral composition.

2. The oral composition of claim 1, wherein the zinc chloride ionizes in solution to produce a 0.02% to about 0.2% by weight concentration of zinc ions in the oral composition and the concentration of the sodium chlorite in the oral composition is from about 0.1% to about 3.0% by weight.

3. The oral composition of claim 1, wherein the zinc chloride ionizes in solution to produce zinc ions at a concentration in the oral composition ranging from about 0.04% to about 0.12% by weight.

4. The oral composition of claim 1, wherein the concentration of the sodium chlorite in the oral composition ranges from about 0.1% to about 1.0% by weight.

5. The oral composition of claim 1, wherein the oral composition is selected from the group consisting of a dental care product, a food product, a lozenge, a chewing gum, and a confection.

6. The oral composition of claim 1, wherein the pH of the first component during storage ranges from about 3.0 to about 6.0 and the pH of the second component during storage ranges from about 7.0 to about 8.5.

7. The oral composition of claim 6, wherein the composition further comprises sodium chloride.

8. The oral composition of claim 1, wherein the pH of the final mixture of the first and second components is about 5.5 to about 6.0.

9. An oral composition comprising a first component containing zinc chloride, which yields freely available zinc ions, and one or more of a zinc-containing compound selected from the group consisting of: zinc sulfate, zinc acetate, zinc lactate, zinc salicylate, zinc nitrate, and a mixture of two or more of the aforementioned zinc-containing compounds in a first vehicle suitable for introduction to the oral cavity and a second component containing sodium chlorite and sodium chloride and a compound selected from the group consisting of hydrogen peroxide, oxyhalogen, methylene blue, and a mixture of two or more of hydrogen peroxide, oxyhalogen, and methylene blue in a second vehicle suitable for introduction to the oral cavity, wherein said first and second components are stored separately and mixed prior to using the oral composition.

10. The oral composition of claim 9, further comprising a pH buffer.

11. The oral composition of claim 10, wherein the pH buffer maintains the pH of the sodium chlorite at between about 7.0 and 8.5.

12. The oral composition of claim 9, wherein the concentration of the sodium chlorite in the oral composition ranges from about 0.1% to about 1.0% by weight.

13. The oral composition of claim 9, wherein the concentration of the chloride ion in the oral composition ranges from about 0.5% to about 3.1% by weight.

14. A method for inhibiting the formation of sulfur containing anions in the oral cavity and preventing a reduction of the oxidation potential of the oral cavity comprising delivering into the oral cavity a therapeutically effective amount of an oral composition, wherein the oral composition comprises a first component containing a zinc chloride, which yields freely available zinc ions, in a first vehicle suitable for introduction to the oral cavity and a second component containing sodium chlorite in a second vehicle suitable for introduction to the oral cavity, wherein said first and second components are stored separately and mixed prior to using the oral composition.

15. The method of claim 14, wherein the zinc chloride ionizes a solution to produce a concentration of zinc ions in the oral composition ranging from about 0.02% to about 0.2% by weight, and wherein the concentration of the sodium chlorite in the oral composition is from about 0.1% to about 3.0% by weight.

16. The method of claim 14, wherein the zinc chloride ionizes in solution to produce zinc ions at a concentration in the oral composition ranging from about 0.04% to about 0.12% by weight.

17. The method of claim 14, wherein the concentration of the sodium chlorite in the oral composition ranges from about 0.1% to about 1.0% by weight.

18. The method of claim 14, wherein the oral composition is selected from the group consisting of a dental care product, a food product, a lozenge, a chewing gum or a confection.

19. The method of claim 14, wherein the pH of the first component during storage ranges from about 3.0 to about 6.0 and the pH of the second component during storage ranges from about 7.0 to about 8.5.

20. The method of claim 19, wherein the composition further comprises sodium chloride.

21. The method of claim 14, wherein the pH of the final mixture of the first and second components is about 5.5 to about 6.0.

22. A method for reducing oral malodor comprising delivering into the oral cavity a therapeutically effective amount of an oral composition, wherein the oral composition comprises a first component containing zinc chloride, which yields freely available zinc ions, in a first vehicle suitable for introduction to the oral cavity and a second component containing sodium chlorite in a second vehicle suitable for introduction to the oral cavity, wherein said first and second components are stored separately and mixed prior to using the oral composition.

23. A method of treating gingivitis-periodontitis comprising delivering into the oral cavity a therapeutically effective amount of an oral composition, wherein the oral composition comprises a first component containing zinc chloride, which yields freely available zinc ions, in a first vehicle suitable for introduction to the oral cavity and a second component containing sodium chlorite in a second vehicle suitable for introduction to the oral cavity, wherein said first and second components are stored separately and mixed prior to using the oral composition.

24. The method of claim 23, wherein the pH of the final mixture of the first and second components is about 5.5 to about 6.0.

25. A kit comprising:
   a. a first aqueous solution containing zinc chloride, which yields freely available zinc ions; and
   b. a second aqueous solution containing sodium chlorite stored separately from the first aqueous solution, wherein the first aqueous solution and the second aqueous solution are adapted to be mixed together to provide an oral composition, suitable for introduction to the oral cavity.

26. The kit of claim 25, wherein the zinc chloride ionizes to produce a zinc ion concentration ranging from about 0.02% to about 0.2% by weight in the first aqueous solution, and wherein the concentration of the sodium chlorite in the second aqueous solution is from about 0.1% to about 3.0% by weight.

27. The kit of claim 25, wherein the zinc chloride ionizes to produce a concentration of zinc ions in the first aqueous solution ranging from about 0.04% to about 0.12% by weight.

28. The kit of claim 25, wherein the concentration of the sodium chlorite in the second aqueous solution ranges from about 0.1% to about 1.0% by weight.

29. The kit of claim 25, wherein the pH of the first aqueous solution during storage ranges from about 3.0 to about 6.0 and the pH of the second aqueous solution during storage ranges from about 7.0 to about 8.5.

30. The kit of claim 25, wherein the first and second aqueous solutions are present in approximately equal amounts.

31. The kit of claim 25, wherein the pH of the final mixture of the first and second components is about 5.5 to about 6.0.

* * * * *